United States Patent
Roux et al.

(10) Patent No.: US 9,597,192 B2
(45) Date of Patent: Mar. 21, 2017

(54) METACARPAL ROD ANCHOR FOR A TRAPEZOMETACARPAL PROSTHESIS

(71) Applicant: Stryker European Holdings I, LLC, Kalamazoo, MI (US)

(72) Inventors: Jean-Luc Roux, Montpellier (FR); Alain Tchurukdichian, Dijon (FR); Gilles Dautel, Nancy (FR); Yann Saint-Cast, Angers (FR)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 14/722,958

(22) Filed: May 27, 2015

(65) Prior Publication Data

US 2015/0342745 A1  Dec. 3, 2015

(30) Foreign Application Priority Data

Jun. 2, 2014 (FR) ...................... 14 54981

(51) Int. Cl.
*A61F 2/42* (2006.01)
*A61F 2/30* (2006.01)

(52) U.S. Cl.
CPC ........ *A61F 2/4241* (2013.01); *A61F 2/30771* (2013.01); *A61F 2/30767* (2013.01);
(Continued)

(58) Field of Classification Search
CPC .. A61F 2/42; A61F 2/4225; A61F 2002/4228; A61F 2002/423; A61F 2002/4233; A61F 2002/4235; A61F 2002/4238; A61F 2/4241; A61F 2002/4243; A61F 2002/4251; A61F 2002/4253; A61F 2002/4256; A61F 2/4261; A61F 2002/4264;
(Continued)

(56) References Cited

U.S. PATENT DOCUMENTS 2,934,065 A * 4/1960 Townley .................. A61F 2/36
 623/23.14
3,462,765 A   8/1969 Swanson
(Continued)

FOREIGN PATENT DOCUMENTS

DE   19651546 A1   6/1997
FR   2883723 A1   10/2006
(Continued)

OTHER PUBLICATIONS

Small Bone Innovations International, Trapezio-metacarpal prosthesis with cup, <www.totlasmallbone.com>, Copyright © 2009.
(Continued)

*Primary Examiner* — Alvin Stewart
(74) *Attorney, Agent, or Firm* — Lerner, David, Littenberg, Krumholz & Mentlik, LLP

(57) ABSTRACT

In one embodiment, the present invention is an anchoring rod that is elongated and tapered, the rod extends from a distal end toward a proximal end, the shape including a palmate side, a dorsal side and lateral sides, is the shape being flared on its palmate side without flaring on its dorsal side and flares on its lateral sides so as to form a flared proximal portion, said flared proximal portion having a substantially trapezoidal cross-section, with a dorsal face larger than the palmate face.

8 Claims, 1 Drawing Sheet

(52) U.S. Cl.
CPC ............... *A61F 2002/3054* (2013.01); *A61F 2002/3092* (2013.01); *A61F 2002/3093* (2013.01); *A61F 2002/30158* (2013.01); *A61F 2002/30332* (2013.01); *A61F 2002/30795* (2013.01); *A61F 2002/30841* (2013.01); *A61F 2002/4258* (2013.01)

(58) Field of Classification Search
CPC ...... A61F 2002/4266; A61F 2002/4269; A61F 2002/4271; A61F 2/3859; A61F 2/3662
See application file for complete search history.

(56) References Cited

U.S. PATENT DOCUMENTS

| | | | |
|---|---|---|---|
| 3,466,669 A | 9/1969 | Flatt | |
| 3,466,670 A * | 9/1969 | Christiansen | A61F 2/36 623/22.43 |
| 3,651,521 A | 3/1972 | Devas | |
| 3,681,786 A | 8/1972 | Lynch | |
| 3,739,403 A | 6/1973 | Nicolle | |
| 3,760,427 A | 9/1973 | Schultz | |
| 3,875,594 A | 4/1975 | Swanson | |
| 3,894,297 A * | 7/1975 | Mittelmeier | A61F 2/36 623/22.14 |
| 3,991,425 A | 11/1976 | Martin et al. | |
| 4,011,603 A | 3/1977 | Steffee | |
| 4,059,854 A | 11/1977 | Laure | |
| 4,101,985 A * | 7/1978 | Baumann | A61F 2/30739 606/67 |
| 4,158,893 A | 6/1979 | Swanson | |
| 4,193,139 A | 3/1980 | Walker | |
| 4,231,121 A | 11/1980 | Lewis | |
| 4,242,759 A | 1/1981 | White | |
| 4,246,660 A | 1/1981 | Wevers | |
| 4,276,660 A | 7/1981 | Laure | |
| 4,279,042 A * | 7/1981 | Andriacchi | A61F 2/36 623/23.15 |
| 4,304,011 A * | 12/1981 | Whelan, III | A61F 2/4241 623/21.16 |
| 4,352,212 A | 10/1982 | Greene et al. | |
| 4,491,987 A * | 1/1985 | Park | A61F 2/30767 623/23.59 |
| 4,655,778 A | 4/1987 | Koeneman | |
| 4,685,919 A | 8/1987 | Niwa et al. | |
| 4,725,280 A | 2/1988 | Laure | |
| 4,790,852 A * | 12/1988 | Noiles | A61B 17/175 623/23.46 |
| 4,871,367 A | 10/1989 | Christensen et al. | |
| 4,944,758 A | 7/1990 | Bekki et al. | |
| 4,955,916 A * | 9/1990 | Carignan | A61F 2/4241 623/21.16 |
| 5,011,497 A | 4/1991 | Persson et al. | |
| 5,037,440 A | 8/1991 | Koenig | |
| 5,041,118 A * | 8/1991 | Wasilewski | A61B 17/1668 606/85 |
| 5,047,059 A * | 9/1991 | Saffar | A61F 2/4241 623/21.15 |
| 5,092,896 A | 3/1992 | Meuli et al. | |
| 5,108,443 A | 4/1992 | Branemark | |
| 5,133,761 A | 7/1992 | Krouskop | |
| 5,147,386 A * | 9/1992 | Carignan | A61F 2/4241 623/21.16 |
| 5,290,314 A | 3/1994 | Koch et al. | |
| 5,405,399 A | 4/1995 | Tornier | |
| 5,405,400 A | 4/1995 | Linscheid et al. | |
| 5,405,401 A | 4/1995 | Lippincott, III et al. | |
| 5,413,609 A | 5/1995 | Nicol et al. | |
| 5,425,777 A | 6/1995 | Sarkisian et al. | |
| 5,458,647 A | 10/1995 | Brochier et al. | |
| 5,458,648 A | 10/1995 | Berman et al. | |
| 5,480,447 A | 1/1996 | Skiba | |
| 5,507,822 A * | 4/1996 | Bouchon | A61F 2/4241 606/62 |
| 5,522,900 A | 6/1996 | Hollister | |
| 5,522,903 A | 6/1996 | Sokolow et al. | |
| 5,549,690 A | 8/1996 | Hollister et al. | |
| 5,580,352 A * | 12/1996 | Sekel | A61F 2/36 606/62 |
| 5,645,605 A * | 7/1997 | Klawitter | A61F 2/4241 623/21.15 |
| 5,674,297 A | 10/1997 | Lane et al. | |
| 5,683,466 A | 11/1997 | Vitale | |
| 5,702,469 A | 12/1997 | Whipple et al. | |
| 5,702,472 A | 12/1997 | Huebner | |
| 5,725,585 A | 3/1998 | Zobel | |
| 5,728,163 A | 3/1998 | Maksene | |
| 5,782,927 A | 7/1998 | Klawitter et al. | |
| 5,824,095 A | 10/1998 | Di Maio, Jr. et al. | |
| 5,938,700 A | 8/1999 | Lippincott, III | |
| 5,976,134 A | 11/1999 | Huebner | |
| 5,976,139 A | 11/1999 | Bramlet | |
| 5,984,970 A | 11/1999 | Bramlet | |
| 5,984,971 A | 11/1999 | Faccioli et al. | |
| 6,053,945 A | 4/2000 | O'Neil et al. | |
| 6,099,571 A | 8/2000 | Knapp | |
| 6,159,247 A | 12/2000 | Klawitter et al. | |
| 6,183,474 B1 | 2/2001 | Bramlet et al. | |
| 6,217,615 B1 | 4/2001 | Sioshansi et al. | |
| 6,217,616 B1 * | 4/2001 | Ogilvie | A61F 2/3804 623/20.11 |
| 6,284,001 B1 | 9/2001 | Knapp | |
| 6,352,560 B1 | 3/2002 | Poeschmann et al. | |
| 6,423,097 B2 | 7/2002 | Rauscher | |
| 6,454,808 B1 * | 9/2002 | Masada | A61F 2/4241 623/21.13 |
| 6,475,242 B1 | 11/2002 | Bramlet | |
| 6,506,215 B1 | 1/2003 | Letot et al. | |
| 6,652,591 B2 * | 11/2003 | Serbousek | A61F 2/367 623/23.15 |
| 6,682,565 B1 | 1/2004 | Krishnan | |
| 6,689,169 B2 * | 2/2004 | Harris | A61F 2/4241 623/21.16 |
| 6,695,844 B2 | 2/2004 | Bramlet et al. | |
| 6,699,292 B2 | 3/2004 | Ogilvie et al. | |
| 6,811,568 B2 * | 11/2004 | Minamikawa | A61F 2/4241 606/63 |
| 6,869,449 B2 | 3/2005 | Ball et al. | |
| 6,984,235 B2 | 1/2006 | Huebner | |
| 6,986,790 B2 * | 1/2006 | Ball | A61F 2/4014 623/19.11 |
| 7,025,789 B2 | 4/2006 | Chow et al. | |
| 7,041,106 B1 | 5/2006 | Carver et al. | |
| 7,160,329 B2 * | 1/2007 | Cooney, III | A61F 2/3804 623/20.11 |
| 7,182,787 B2 | 2/2007 | Hassler et al. | |
| 7,494,509 B1 * | 2/2009 | Hershberger | A61F 2/3662 623/22.4 |
| 7,611,538 B2 | 11/2009 | Belliard et al. | |
| 7,641,696 B2 | 1/2010 | Ogilvie et al. | |
| 7,736,809 B2 | 6/2010 | Hwang et al. | |
| 7,740,661 B2 * | 6/2010 | Baratz | A61F 2/3804 623/20.11 |
| 7,780,737 B2 * | 8/2010 | Bonnard | A61F 2/4225 623/21.11 |
| 7,837,738 B2 * | 11/2010 | Reigstad | A61B 17/1686 623/21.11 |
| 7,837,739 B2 | 11/2010 | Ogilvie | |
| 7,857,859 B2 * | 12/2010 | Willi | A61F 2/3609 623/22.42 |
| 7,879,106 B2 * | 2/2011 | McMinn | A61F 2/3859 623/22.44 |
| 7,896,919 B2 | 3/2011 | Belliard et al. | |
| 7,976,580 B2 * | 7/2011 | Berger | A61F 2/4241 623/21.13 |
| 8,012,217 B2 * | 9/2011 | Strzepa | A61F 2/4202 623/21.18 |
| 8,021,431 B1 * | 9/2011 | Townley | A61F 2/4241 623/21.11 |
| 8,034,116 B2 * | 10/2011 | Vander Meulen | A61F 2/3804 623/18.11 |

(56) References Cited

U.S. PATENT DOCUMENTS

| | | | |
|---|---|---|---|
| 8,043,375 B2* | 10/2011 | Strzepa | A61F 2/30756 623/14.12 |
| 8,052,755 B2* | 11/2011 | Naidu | A61F 2/3804 623/21.12 |
| 8,070,786 B2 | 12/2011 | Huebner et al. | |
| 8,088,168 B2 | 1/2012 | Hassler et al. | |
| 8,092,530 B2 | 1/2012 | Strzepa et al. | |
| 8,100,983 B2 | 1/2012 | Schulte | |
| 8,133,283 B2 | 3/2012 | Wilson | |
| 8,152,847 B2 | 4/2012 | Strzepa et al. | |
| 8,167,952 B2 | 5/2012 | Graham et al. | |
| 8,167,953 B2 | 5/2012 | Warburton | |
| 8,177,842 B2 | 5/2012 | Strzepa et al. | |
| 8,177,852 B2* | 5/2012 | Mcminn | A61F 2/3859 623/22.44 |
| 8,226,721 B2 | 7/2012 | Belliard et al. | |
| 8,231,625 B2 | 7/2012 | Graham et al. | |
| 8,292,966 B2 | 10/2012 | Morton | |
| 8,303,666 B2 | 11/2012 | Vanasse | |
| 8,343,228 B2 | 1/2013 | Graham | |
| 8,366,785 B1 | 2/2013 | Townley | |
| 8,377,142 B2 | 2/2013 | Trail et al. | |
| 8,394,097 B2 | 3/2013 | Peyrot et al. | |
| 8,414,583 B2 | 4/2013 | Prandi et al. | |
| 8,475,456 B2 | 7/2013 | Augoyard et al. | |
| 8,491,663 B2 | 7/2013 | Lindner et al. | |
| 8,506,641 B2 | 8/2013 | Graham et al. | |
| 8,529,632 B2* | 9/2013 | Klawitter | A61F 2/4241 623/21.15 |
| 8,617,251 B2 | 12/2013 | Calandruccio et al. | |
| 8,628,581 B2 | 1/2014 | Zang et al. | |
| 8,628,582 B2 | 1/2014 | Lavi | |
| 8,641,770 B2 | 2/2014 | Scheker | |
| 8,647,390 B2* | 2/2014 | Bellemere | A61F 2/4241 606/63 |
| 8,747,480 B2 | 6/2014 | Cachia | |
| 8,808,391 B2* | 8/2014 | Mcminn | A61F 2/3601 623/22.44 |
| 8,945,232 B2 | 2/2015 | Sander et al. | |
| 9,034,048 B2 | 5/2015 | Choren | |
| 2002/0003021 A1 | 1/2002 | Maxton et al. | |
| 2002/0004258 A1 | 1/2002 | Nakayama et al. | |
| 2002/0004271 A1 | 1/2002 | Weis | |
| 2002/0004276 A1 | 1/2002 | Ahn et al. | |
| 2002/0030649 A1 | 3/2002 | Zavracky et al. | |
| 2003/0040805 A1* | 2/2003 | Minamikawa | A61F 2/4241 623/23.46 |
| 2003/0074083 A1* | 4/2003 | LeGros | A61F 2/3601 623/23.35 |
| 2004/0023119 A1 | 2/2004 | Mizutani et al. | |
| 2005/0085921 A1* | 4/2005 | Gupta | A61F 2/4261 623/21.13 |
| 2005/0137713 A1* | 6/2005 | Bertram, III | A61F 2/38 623/23.44 |
| 2005/0147857 A1 | 7/2005 | Crumm et al. | |
| 2005/0256585 A1* | 11/2005 | Park | A61F 2/3603 623/23.14 |
| 2006/0115735 A1 | 6/2006 | Yasuda et al. | |
| 2006/0167557 A1* | 7/2006 | Terrill | A61F 2/3609 623/22.43 |
| 2007/0134549 A1 | 6/2007 | Nathan et al. | |
| 2007/0243456 A1 | 10/2007 | Ahn et al. | |
| 2008/0065224 A1* | 3/2008 | Reigstad | A61B 17/1686 623/18.11 |
| 2008/0091274 A1* | 4/2008 | Murphy | A61F 2/3609 623/22.42 |
| 2008/0131784 A1 | 6/2008 | Hwang et al. | |
| 2008/0133023 A1* | 6/2008 | Schlotterback | A61F 2/3609 623/22.42 |
| 2008/0137890 A1 | 6/2008 | Petersen et al. | |
| 2008/0200990 A1* | 8/2008 | McTighe | A61F 2/36 623/22.42 |
| 2008/0241689 A1 | 10/2008 | Takami et al. | |
| 2008/0268338 A1 | 10/2008 | Lee et al. | |
| 2009/0107746 A1 | 4/2009 | Horie et al. | |
| 2009/0254190 A1 | 10/2009 | Gannoe et al. | |
| 2010/0010637 A1 | 1/2010 | Pequignot | |
| 2011/0112652 A1* | 5/2011 | Hansson | A61F 2/4241 623/21.16 |
| 2011/0172782 A1 | 7/2011 | Klawitter et al. | |
| 2011/0251697 A1* | 10/2011 | Chung | A61F 2/30771 623/23.15 |
| 2011/0274954 A1 | 11/2011 | Cho et al. | |
| 2013/0053974 A1* | 2/2013 | Shultz | A61F 2/4261 623/21.12 |
| 2013/0338784 A1* | 12/2013 | Pallia | A61F 2/4241 623/21.13 |
| 2014/0018930 A1 | 1/2014 | Oster | |
| 2014/0094927 A1* | 4/2014 | Weeden | A61F 2/32 623/22.21 |
| 2014/0100664 A1* | 4/2014 | Leibel | A61F 2/4261 623/21.13 |
| 2015/0305788 A1* | 10/2015 | Hansson | A61F 2/4241 606/328 |
| 2015/0342745 A1* | 12/2015 | Roux | A61F 2/30771 623/21.15 |

FOREIGN PATENT DOCUMENTS

| | | |
|---|---|---|
| FR | 2912051 A1 | 8/2008 |
| GB | 2308068 A | 6/1997 |
| JP | 2007087789 A | 4/2007 |
| JP | 2008243612 A | 10/2008 |
| JP | 2010-129412 A | 6/2010 |
| KR | 2005-0030438 A | 3/2005 |
| KR | 20050099903 A | 10/2005 |
| KR | 20070009231 A | 1/2007 |
| KR | 10-0742739 B1 | 7/2007 |
| KR | 100804411 B1 | 2/2008 |
| KR | 20080067371 A | 7/2008 |
| KR | 20090009598 A | 1/2009 |
| WO | 2005098994 A1 | 10/2005 |
| WO | 2009014299 A1 | 1/2009 |
| WO | 2010076975 A2 | 7/2010 |

OTHER PUBLICATIONS

Extended European Search Report for Application No. EP15170166 dated Jul. 17, 2015.

* cited by examiner

METACARPAL ROD ANCHOR FOR A TRAPEZOMETACARPAL PROSTHESIS

CROSS-REFERENCE TO RELATED APPLICATIONS

The present application claims priority from French application no. 1454981 filed on Jun. 2, 2014, the disclosure of which is hereby incorporated herein by reference.

BACKGROUND OF THE INVENTION

The present invention relates to a metacarpal anchoring rod, particularly for a trapezo-metacarpal prosthesis. It also relates to a set of modular elements allowing the constitution of such a trapezo-metacarpal prosthesis.

It is well known to restore a trapezo-metacarpal articulation by means of a prosthesis, which can either include only a metacarpal prosthetic element, implanted in the first metacarpal and coming directly into articulation with the trapezium bone, or to include both an metacarpal prosthetic element and a trapezium prosthetic element, each element being implanted in its corresponding bone and coming into articulation with the other element.

The metacarpal element often consists of two parts assembled one to the other, to with an elongated and tapered part constituting an anchoring rod to the first metacarpal and an articulation part forming an articulating surface.

A trapezo-metacarpal prosthesis can in any case be of the type called "anatomical," wherein prosthetic articulation surface(s) reproduce more or less the shape of the native articulation surface(s), which have an aspect in the form of a "saddle"; they can also be of the type called "guided," wherein the articulation of the prosthetic elements is accomplished by means of a ball formed by a spherical head forming a part of the metacarpal element and by a receiving cup accommodating this spherical head, the cup constituting the trapezium element.

The anchoring rods which are formed by the metacarpal elements of the known prostheses have the considerable disadvantage of not presenting a shape that is perfectly adapted to that of the marrow channel of the first metacarpal. Moreover, the more or less conical form of the marrow channel of this first metacarpal can have a certain tendency to eject such an anchoring rod.

BRIEF SUMMARY OF THE INVENTION

The present invention has as its objective to correct these essential disadvantages.

The anchoring rod concerned is, in a manner known in se, elongated and tapered.

According to the invention, this anchoring rod, from its distal end to its proximal end, flares on its palmate side without flaring on its dorsal side and flares on its lateral sides, so as to form a proximal flared portion, said flared proximal portion having a substantially trapezoidal transverse section, with a dorsal face wider than the palmate face.

The anchoring rod thus shaped proves to have a perfect stability of mounting in a metacarpal, in particular the first metacarpal.

It will be understood that the term "distal" qualifies the end of the anchoring rod which, after implantation, is the farthest away from the heart, the term "proximal" qualifying the end of the anchoring rod closest to the heart after this implantation. Likewise, the terms "palmate" and "dorsal" designate the sides or faces of the anchoring rod which, after implantation, are respectively turned to the palmate side and to the dorsal side of the hand, and the term "laterals" employed below qualifies the faces of the rod turned toward the respectively left and right sides of the hand after implantation.

Preferably, said palmate face has a curve extending from an area near the distal end of the anchoring rod to the edges of said proximal end of this rod.

This curve of the face contributes to ensure a perfect seat of the anchoring rod in the marrow channel of a metacarpal, in particular of the first metacarpal, at the metaphyseal part of the last mentioned.

According to one preferred embodiment of the invention, the anchoring rod has a rounded boss on its palmate side, in proximity to its distal end.

This boss is capable of impressing itself into the sponge-like bone of the metacarpal when the anchoring rod is inserted into the marrow channel of this metacarpal, thus realizing, in combination with the aforementioned form of the anchoring rod, an anti-ejection effect for that rod.

Preferably, the rod has, at the proximal side of said flared proximal portion, rounded ridges situated between the dorsal, palmate and lateral faces of this rod.

The rounded nature of these ridges makes it possible to avoid the use of supports against the cortical bone that are too localized.

The rounded ridges which separate each lateral face from the palmate face can rejoin each other on the palmate side of the anchoring rod, so that each palmate face has, seen in transverse section, a rounded shape on the proximal side of said flared proximal portion.

Preferably, the anchoring rod has grooves provided in its lateral faces, with a "wolf's teeth" profile, that in to say that each groove delimits, on its face turned toward said distal end, a steep wall flank, more or less perpendicular to the longitudinal axis of the anchoring rod and, on its side turned toward said proximal end, an inclined wall flank.

The steep wall flanks constitute support surfaces effectively opposing the ejection of the anchoring rod out of the marrow channel of the metacarpal.

According to one preferred embodiment of the invention in this case, the anchoring rod includes, on each lateral face, two grooves such as those aforementioned at its flared proximal portion, near one another, and a groove at its distal portion.

Advantageously, the anchoring rod includes a porous bone-inducing covering, particularly accomplished by projection onto the rod of particles of titanium by means of a plasma torch.

The assembly of modular elements according to the invention includes:
  said anchoring rod, which includes a cavity for assembly provided in its proximal end, said cavity being formed by a slightly conical principal portion and by a groove extending radially from that principal portion;
  a first articulation part capable of being assembled to that anchoring rod to constitute a metacarpal element of a first type, said first articulation part including a spherical articulation head and an assembly pin of slightly conical shape, capable of being received in said principal portion of the assembly cavity and to be retained in this principal position by wedging;
  a second articulation part capable of being assembled to said anchoring rod to constitute a metacarpal element of a second type, forming an anatomical articulate surface and including an assembly pin having a slightly conical principal portion and a rib extending radially from this principal portion, this principal portion and this rib being designed to be accommodated respectively in said principal portion of the assembly cavity and in said groove which is formed by said cavity, and said principal portion of the assembly pin being designed to be retained in said principal portion of the assembly cavity by wedging.

This assembly of modular elements thus makes it possible to form at will, including during the operation, either a prosthesis of the "guided" type, by the use of said first articulation part, or a prosthesis of the "anatomical" type, through the use of said second articulation part. In the first case, the pin of said first articulation part is simply slipped over said principal portion of the cavity; the assembly of elements then includes a receiving cup accommodating the spherical head which forms this first articulation part, this cup being designed to be anchored in the trapezium bone. In the second case, said rib of the pin of said second articulation part and said groove of the cavity make it possible to ensure the adequate angular mounting of this second articulation part with respect to the anchoring rod, so that the correct positioning of this second articulation part with respect to this anchoring rod is provided for.

The invention will be well understood, and other characteristics and advantages of it will appear, with reference to the appended schematic drawing, this drawing showing, by way of a non-limiting example, a preferred embodiment of a trapezo-metacarpal articulation prosthesis including the rod in question which, shown in this example, is a prosthesis of the "guided" type.

DETAILED DESCRIPTION

Figure 1:
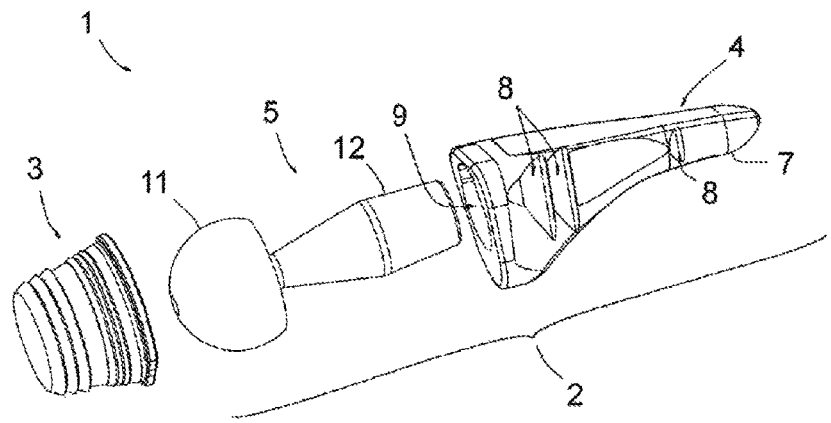
FIG. 1 is a view in exploded perspective.

FIG. 1 shows a trapezo-metacarpal prosthesis 1 including a metacarpal element 2 and a trapezium element 3.

The metacarpal element 2 is formed by the assembly of an anchoring rod 4 and an articulation part 5.

Figure 5:
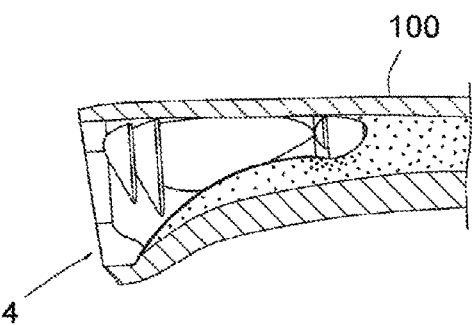
FIG. 5 is a view of the anchoring rod similar to FIG. 2, after placement of this rod in the first metacarpal.

The metacarpal element 2 is designed to be anchored to the first metacarpal 100 by insertion of the rod 4 into the marrow channel of this first metacarpal 100, as can be seen in FIG. 5. The rod 4 has, to this end, between its proximal end 4p and its distal end 4d, an elongated and tapered shape.

Figure 2:
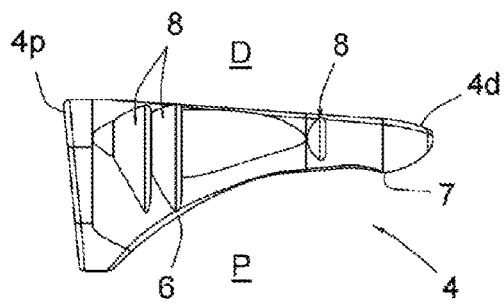
FIG. 2 is a side view of an anchoring rod which includes this prosthesis.
Figure 4:
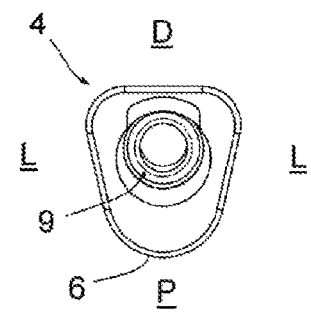
FIG. 4 is a view of this anchoring rod at the end, by the proximal end of said rod.
Figure 3:
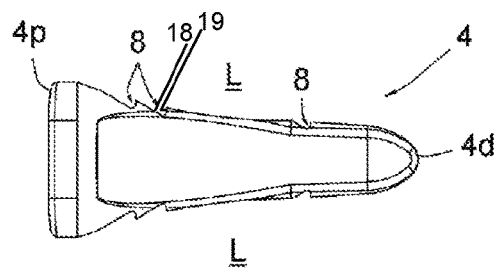
FIG. 3 is a view of this anchoring rod from the dorsal side of said rod.

As is visible on FIGS. 2 to 4, from this distal end 4d to this proximal end 4p, the rod 4 flares on its palmate side P without flaring on its dorsal side D, and flares on its lateral sides L. It thus forms a flared proximal portion offset on the palmate side P, which has a substantially trapezoidal cross-section, with a dorsal face that is larger than the palmate face, the two lateral faces of this portion consequently converging one toward the other in the direction of the palmate side P, as can be seen in FIG. 4.

The ridges separating the dorsal face and the lateral faces, as well as the ridges separating the palmate face 6 and the lateral faces, are rounded at the proximal side of said proximal flared portion, see FIG. 4; the rounded ridges which separate each lateral face and the palmate face 6 rejoin each other on the palmate side P of the rod 4, such that said palmate face has a rounded section on this proximal side of said flared proximal portion.

The palmate face 6 has moreover a curved shape from an area near the distal end 4d to the edges of the proximal end 4p, as shown in FIG. 2.

The anchoring rod 4 also shows a rounded boss 7 on its palmate side P, located in proximity to its distal end 4d, and grooves 8 provided in its lateral faces, with a "wolf teeth" profile (see FIG. 3). Each groove 8 thus delimits, on its edge turned toward the distal end 4d, a steep wall flank 19, more or less perpendicular to the longitudinal axis of the anchoring rod 4, and on its side turned toward the proximal end 4p, an inclined wall flank 18.

The anchoring rod 4 also includes a cavity 9 provided in its proximal end 4p, to assemble it to the articulation part 5. This cavity 9 is formed by a slightly conical principal portion and by a groove extending radially from this principal portion, on the dorsal side of the rod 4 in the example shown.

The anchoring rod 4 also includes, outside of its proximal face, a porous bone-inducing covering, accomplished by projecting particles of titanium onto it by means of a plasma torch.

The articulation part 5 includes a spherical articulation head 11 and a pin 12 of slightly conical form, this pin 12 being designed to be received in said principal portion of the cavity 9 and retained in that principal portion by wedging, so as to accomplish the assembly of the articulation part 5 into the anchoring rod 4 and to thus form the metacarpal element 2.

The trapezium element 3, for its part, is constituted by a cup having on the outside anchoring ribs into the trapezium bone and forming interiorly an articulating cavity, designed to accommodate the head 11.

In practice, as shown by FIG. 5, the anchoring rod 4 is pushed into the sponge-like bone of the first metacarpal 100 up to complete engagement of its flared proximal portion into the proximal end of this bone. In this position, this flared proximal portion is in adequacy with this proximal end of the first metacarpal, and the dorsal face of the rod 4 extends along the dorsal cortical bone and the curved palmate face 6 has a large support on the endo-cortical, ensuring a perfect seat of the rod 4 in the marrow channel of the first metacarpal 100. On the distal side, the boss 7 impresses itself into the sponge-like bone, thus accomplishing, in combination with the aforementioned shape of the rod 4 and with its aforementioned steep wall flanks, an anti-ejection function for that rod.

Once the rod 4 is in place on the first metacarpal 100 as shown in FIG. 5, the articulation part 5 is put in place on the rod 4 so as to constitute the metacarpal element 2 of the prosthesis 1, by insertion of the pin 12 into the cavity 9, then the head 11 is engaged in the cavity of the trapezium element 3, put in place on the trapezium bone.

It should be noted that the elements 3, 4, 5 are part of a set of elements including, besides several sizes of rods 4, a second articulation part forming an anatomic articulation surface, that is, reproducing more or less the shape of the native articulate surface(s), as a "saddle"; this second articulation part includes an assembly pin having a slightly conical principal portion, capable of being accommodated and wedged in the principal portion of the cavity 9, and a rib extending radially from this principal portion, capable of being engaged in the groove that this cavity 9 forms. The adequate angular mounting of said second articulation part with respect to the anchoring rod 4 is thus ensured.

Said assembly of elements thus makes it possible to form, as desired, including during the operation, either a prosthesis of the "guided" type as shown in the figures, by the use of the articulation part 5, or a prosthesis of the "anatomical" type, by the use of said second articulation part.

As shown by the foregoing, the invention provides a metacarpal rod, particularly for a trapezo-metacarpal prosthesis, which has, with respect to the homologous rods of the prior art, the determinant advantages of having a perfect seat in a metacarpal, to have a low tendency to ejection out of said bone, and to allow the adequacy of numerous articulated interfaces.

The invention claimed is:

1. A metacarpal anchoring rod, particularly for a trapezo-metacarpal prosthesis, comprising an elongated and tapered shape extending from a distal end toward a proximal end, the shape including a palmate side, a dorsal side and lateral sides, the shape being flared on its palmate side without flaring on its dorsal side and flares on its lateral sides so as to form a flared proximal portion, said flared proximal portion having a substantially trapezoidal cross-section, with a dorsal face larger than the palmate face, wherein the lateral faces include grooves formed within the lateral faces, each groove delimiting, on its side turned toward said distal end, a steep wall flank, generally perpendicular to a longitudinal axis of the anchoring rod and, on its side turned toward said proximal end, an inclined wall flank; wherein a distal portion includes a boss with a rounded shape positioned on the palmate side.

2. The rod according to claim 1, wherein said palmate face has a curvature extending from an area near its distal end up to the edges of its proximal end.

3. The rod according to claim 2, wherein the shape has a rounded boss on its palmate side, in proximity to its distal end.

4. The rod according to one of claim 1, wherein the proximal side of said flared proximal portion includes more than one rounded ridge situated between the dorsal, palmate and lateral faces.

5. The rod according to claim 4, wherein the rounded ridges which separate each lateral face and the palmate face rejoin one another on the palmate side of the anchoring rod, such that said palmate face has, seen in cross-section, a rounded shape on the proximal side of said flared proximal portion.

6. The rod according to claim 1, wherein each lateral face includes two grooves at its flared proximal portion, and another groove at its distal portion.

7. The rod (4) according to one of claim 1, further comprising a porous bone inducing covering.

8. A set of modular elements allowing the constitution of a trapezo-metacarpal prosthesis including an anchoring rod according to one of claim 1, wherein:

said anchoring rod includes an assembly cavity provided in its proximal end, this cavity having a slightly conical principal portion and a groove which extends radially from the principal portion of the assembly cavity;

said set of elements includes a first articulation part capable of being assembled to this anchoring rod to constitute a metacarpal element of a first type, this first articulation part including a spherical articulation head and an assembly pin of slightly conical shape, capable of being accommodated in said principal portion of the assembly cavity and to be retained in this principal portion by wedging;

said set of elements includes a second articulation part capable of being assembled to said anchoring rod to constitute a metacarpal element of a second type, forming an anatomical articulation surface and including an assembly pin having a slightly conical principal portion and a rib extending radially from the principal portion of the assembly pin, the principal portion and rib of the assembly pin being designed to be received respectively in said principal portion of the assembly cavity and in said groove which forms said cavity, and said principal portion of the assembly pin being intended to be retained in said principal portion of the assembly cavity by wedging.

\* \* \* \* \*